United States Patent
Mansouri

(10) Patent No.: US 9,192,673 B2
(45) Date of Patent: Nov. 24, 2015

(54) FINE DRY PARTICULATE RESVERATROL ACTIVE AGENT COMPOSITIONS AND TOPICAL FORMULATIONS INCLUDING THE SAME

(71) Applicant: Laboratory Skin Care, Inc., Tahoe City, CA (US)

(72) Inventor: Zahra Mansouri, Tahoe City, CA (US)

(73) Assignee: Laboratory Skin Care, Inc., South San Francisco, CA (US)

(*) Notice: Subject to any disclaimer, the term of this patent is extended or adjusted under 35 U.S.C. 154(b) by 0 days.

(21) Appl. No.: 14/214,456

(22) Filed: Mar. 14, 2014

(65) Prior Publication Data

US 2014/0271880 A1  Sep. 18, 2014

Related U.S. Application Data

(60) Provisional application No. 61/798,727, filed on Mar. 15, 2013.

(51) Int. Cl.
*A61K 47/02* (2006.01)
*A61K 31/05* (2006.01)
*A61K 9/00* (2006.01)

(52) U.S. Cl.
CPC .............. *A61K 47/02* (2013.01); *A61K 9/0014* (2013.01); *A61K 31/05* (2013.01)

(58) Field of Classification Search
CPC ...... A61K 9/0014; A61K 31/05; A61K 47/02
See application file for complete search history.

(56) References Cited

U.S. PATENT DOCUMENTS

| | | | |
|---|---|---|---|
| 4,948,575 A | 8/1990 | Cole et al. | |
| 5,055,307 A * | 10/1991 | Tsuru et al. | 424/493 |
| 5,158,756 A | 10/1992 | Ogawa et al. | |
| 5,604,200 A | 2/1997 | Taylor-McCord | |
| 6,096,324 A | 8/2000 | Mansouri | |
| 6,120,782 A | 9/2000 | Mansouri | |
| 6,262,020 B1 | 7/2001 | Lezday et al. | |
| 6,395,311 B2 | 5/2002 | Jia | |
| 6,573,249 B2 | 6/2003 | Lezday et al. | |
| 8,080,583 B2 * | 12/2011 | Maes et al. | 514/513 |

(Continued)

FOREIGN PATENT DOCUMENTS

| | | |
|---|---|---|
| CN | 1813657 A | 8/2006 |
| WO | WO 2010/039560 A2 | 4/2010 |
| WO | WO 2010/129819 A2 | 11/2010 |

OTHER PUBLICATIONS

Meisel M., "About Face, Anti-aging, natural products lead the thriving skin care category" Happi Household and Personal Products Industry. (May 7, 2008) web article: http:// www.happi.com/articles/2008/05/about-face; 15 pp.

*Primary Examiner* — Jane C Oswecki

(74) *Attorney, Agent, or Firm* — Bret E. Field; Bozicevic, Field & Francis LLP

(57) ABSTRACT

Fine dry particulate resveratrol compositions suitable for use in topical formulations, as well as methods of making the same, are provided. In the dry particulate resveratrol composition, the resveratrol active agent is associated with the particles, e.g., via entrapment in the pores of the particles and/or ionic binding and/or non-covalent binding to the surface of the particles and/or loosely associated with the particles. Also provided are topical formulations which include the dry particulate resveratrol compositions of the invention, and methods of using the same.

11 Claims, 1 Drawing Sheet

(56) References Cited

U.S. PATENT DOCUMENTS

| | | |
|---|---|---|
| 2001/0006680 A1 | 7/2001 | Mansouri |
| 2002/0018797 A1 | 2/2002 | Cui et al. |
| 2002/0086055 A1 | 7/2002 | Wong et al. |
| 2003/0077235 A1 | 4/2003 | Mansouri |
| 2005/0013874 A1 | 1/2005 | Ito et al. |
| 2005/0234114 A1 | 10/2005 | Lee |
| 2005/0271694 A1 | 12/2005 | Mansouri et al. |
| 2006/0093670 A1 | 5/2006 | Mizushima et al. |
| 2006/0193879 A1 | 8/2006 | Mansouri |
| 2006/0257658 A1 | 11/2006 | Tanaka et al. |
| 2007/0003487 A1 | 1/2007 | Ek |
| 2008/0051335 A1 | 2/2008 | Kleiner et al. |
| 2008/0220233 A1 | 9/2008 | Kjellin et al. |
| 2009/0035236 A1 | 2/2009 | Maes et al. |
| 2009/0035240 A1 | 2/2009 | Maes et al. |
| 2009/0035242 A1 | 2/2009 | Maes et al. |
| 2009/0035243 A1 | 2/2009 | Czarnota et al. |
| 2009/0074688 A1 | 3/2009 | Mansouri |
| 2009/0099651 A1 | 4/2009 | Hakimi-Mehr et al. |
| 2009/0104133 A1 | 4/2009 | Mansouri |
| 2010/0086606 A1 | 4/2010 | Ogawa |
| 2012/0130435 A1 | 5/2012 | Hart et al. |
| 2012/0134919 A1 | 5/2012 | Engqvist et al. |
| 2012/0207803 A1 | 8/2012 | Bell |

* cited by examiner

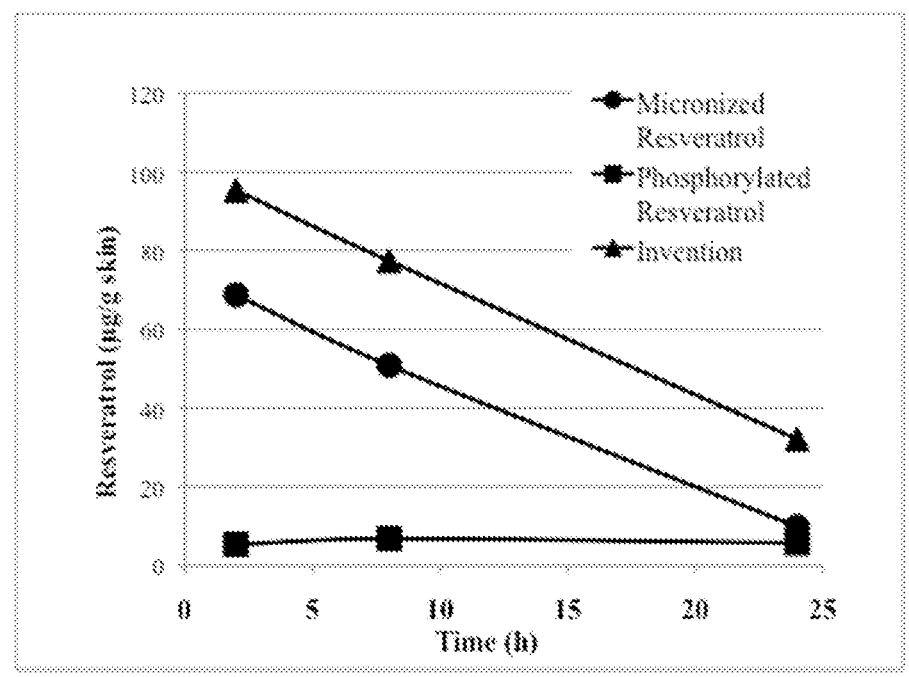

FINE DRY PARTICULATE RESVERATROL ACTIVE AGENT COMPOSITIONS AND TOPICAL FORMULATIONS INCLUDING THE SAME

CROSS-REFERENCE TO RELATED APPLICATIONS

Pursuant to 35 U.S.C. §119(e), this application claims priority to the filing date of U.S. Provisional Patent Application Ser. No. 61/798,727 filed Mar. 15, 2013; the disclosure of which application is herein incorporated by reference.

INTRODUCTION

Skin includes a surface layer, known as the epidermis, and a deeper connective tissue layer, known as the dermis. The epidermis undergoes continuous turnover as the outermost cells are exfoliated and replaced by cells that arise from inner dermal layers. The dermis is composed of a variety of cell types, including fibroblasts.

Skin thickness begins to decline in humans after the age of 20 as the dermis becomes thinner and the number of skin fibroblasts declines. As skin ages, or is exposed to UV light and other environmental insults, changes in the underlying dermis can lead to the functional and morphological changes associated with damaged skin. Decreases in the abundance and function of products of the fibroblasts, which include collagen and proteoglycans, are believed to play major roles in wrinkled and damaged skin.

Resveratrol, also referred to as 3,5,4'-trihydroxystilbene, is a polyhydroxy-substituted compound having the general formula:

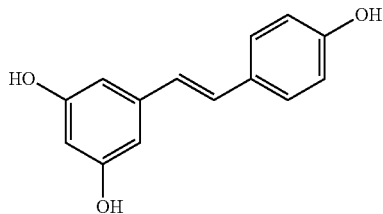

It is present in red grapes, raspberries, blueberries, and certain other plant berries or extracts. It has been reported that resveratrol has anti-aging, anti-cancer, and antiviral effects. Because of its beneficial properties, resveratrol has been incorporated into a variety of cosmetic formulations, such as skin creams. However, one problem with resveratrol is that it is generally unstable in cosmetic formulations. Accordingly, if used in cosmetic formulas, it can only be used in very small amounts. If present in too large an amount, the resveratrol will hydrolyze and cause the cosmetic formulation into which it is incorporated to become discolored. The compound has stability issue-sensitive to light and heat, solubility problem-almost insoluble in water and in lipophilic components, and bioavailability issues-do not reach in vivo a sufficient effect because of their poor solubility, which may limit its use in foods and supplements, and cosmetic applications.

SUMMARY

Fine dry particulate resveratrol compositions suitable for use in topical formulations, as well as methods of making and using the same, are provided. In the dry particulate resveratrol composition, the resveratrol active agent is associated with the particles, e.g., via entrapment in the pores of the particles and/or ionic binding and/or non-covalent binding to the surface of the particles and/or loosely associated with the particles. Also provided are topical formulations which include the dry particulate resveratrol compositions of the invention, and methods of using the same.

BRIEF DESCRIPTION OF THE FIGURES

FIG. 1 provides graphical results of a study showing the improved delivery into skin.

DETAILED DESCRIPTION

Fine dry particulate resveratrol compositions suitable for use in topical formulations, as well as methods of making the same, are provided. In the dry particulate resveratrol composition, the resveratrol active agent is associated with the particles, e.g., via entrapment in the pores of the particles and/or ionic binding and/or non-covalent binding to the surface of the particles and/or loosely associated with the particles. Also provided are topical formulations which include the dry particulate resveratrol compositions of the invention, and methods of using the same.

Before the present invention is further described, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods of Making Fine Dry Particulate Actives and Fine Dry Particulate Actives Produced Using the Same As summarized above, aspects of the invention include methods of making fine dry particulate resveratrol compositions, where the methods include combining an amount of nanoporous calcium particles (e.g., calcium phosphate particles) and one or more resveratrol active agents in a manner sufficient to produce a dry particulate resveratrol composition. As reviewed above, in the dry particulate resveratrol compositions, the active agent is associated with the particles, e.g., via entrapment in the pores of the particles and/or ionic binding and/or non-covalent binding to the surface of the particles and/or loosely associated with the particles. In practicing methods according to embodiments of the invention, nanoporous calcium particles and one or more resveratrol active agents are combined in the presence of a suitable solvent system under conditions sufficient for the active agent(s) to enter internal space of the particles and/or ionically bind and/or covalently bind and/or associate with the surface of the particles. Before further describing the method steps, the particles, active agents and solvent systems employed in certain embodiments of the methods are reviewed in greater detail.

Nanoporous Calcium Particles

Particles employed in methods of the invention are nanoporous phosphate particles. By "nanoporous" is meant that the particles have a porosity of 30% or more, such as 40% or more, including 50% or more, where the porosity may range from 30% to 85%, such as from 40% to 70%, including from 45% to 55%, as determined using a mercury intrusion porosimeter porosity determination protocol as described in ASTM D 4284-88 "Standard Test Method for Determining Pore Volume Distribution of Catalysts by Mercury Intrusion Porosimetry". Porosity is also described by "pore volume (ml/g)" and in such instances many range from 0.1 ml/g to 2.0 ml/g. In some cases, the particles have a porosity such that their internal surface area ranges from 10 $m^2/g$ to 150 $m^2/g$, such as from 20 $m^2/g$ to 100 $m^2/g$, including 30 $m^2/g$ to 80 $m^2/g$, as determined using a BET gas adsorption surface area determination protocol as described in ASTM D3663-03 Standard Test Method for Surface Area of Catalysts and Catalyst Carriers. The pore diameter may vary, ranging in certain instances from 2 to 100 nm, such as 5 to 80 nm, including 10 to 60 nm. In addition, the particles may have a tapping density ranging from 0.2 $g/cm^3$ to 0.5 $g/cm^3$, such as from 0.25 $g/cm^3$ to 0.45 $g/cm^3$, including from 0.3 $g/cm^3$ to 0.4 $g/cm^3$. The tap density can be measured by using standard ASTM WK13023—New Determination of Tap Density of Metallic Powders by a Constant Volume Measuring Method.

In some instances, the particles are rigid particles which are uniform and spherical in shape. By "rigid" is meant that the particles are hard, such that they are not pliant. By "uniform" is meant that the shape of the particles does not vary substantially, such that the particles have substantially the same spherical shape. The term "spherical" is employed in its conventional sense to mean a round body whose surface is at all points substantially equidistant from the center. Of interest in certain embodiments are calcium particles having a diameter of 20 μm or less, such as 10 μm or less, including 5 μm or less, where in some instances the medium diameter is 4 μm or less, such as 3 μm or less, including 2 μm or less. Of interest in certain embodiments are calcium particulate compositions in which the median diameter of the all of the particle members in the composition is 20 μm or less, such as 10 μm or less, including 5 μm or less, where in some instances the medium diameter is 4 μm or less, such as 3 μm or less, including 2 μm or less. Of interest in certain embodiments are calcium particulate compositions in which the arithmetic mean or average of all of the particles in the composition is 20 μm or less, such as 10 μm or less, including 5 μm or less, where in some instances the medium diameter is 4 μm or less, such as 3 μm or less, including 2 μm or less. With respect to the above ranges, in some instances the particles have a diameter of 0.1 μm or greater, such as 0.05 μm or greater, including 1.0 μm or greater.

The particles are, in some instances, chemically pure. By chemically pure is meant that the particles are made up of substantially one type of compound, e.g., a calcium compound, such as a calcium phosphate mineral. Of interest as porous particles are calcium containing particles, such as calcium containing particles that are made of a molecule that includes calcium cation and a suitable anion, e.g., carbonate, phosphate, etc. In some instances, the particles are calcium carbonate particles, such as but not limited to the calcium carbonate particles disclosed in U.S. Pat. Nos. 5,292,495 and 7,754,176. In some instances, the calcium phosphate particles are made up of a calcium phosphate that is described by the molecular formula $Ca_{10}(PO_4)_6(OH)_2$.

In some instances, the particles are ceramic particles. By ceramic is meant that the particles are produced using a method which includes a step of subjecting the particles to high temperature conditions, where such conditions are illustrated below. High temperatures may range from 200 to 1000° C., such as 300 to 900° C. and including 300 to 800° C. In some embodiments, the particles have a compression rupture strength ranging from 20 to 200 MPa, such as from 50 to 150 MPa, and including 75 to 90 MPa, as determined using a SHIMADZU MCT-W500 micro-compression testing machine particle strength determination protocol with a particle sintered at temperature of 400° C. to 900° C., as described in European Patent EPI 840661. In some embodiments, the particles are biodegradable, by which is meant that the particles degrade in some manner, e.g., dissolve, over time under physiological conditions. As the particles of these embodiments are biodegradeable under physiological conditions, they at least begin to dissolve at a detectable rate under conditions of pH of 5.8 or less, such as 5.5 or less, e.g., 5.3 or less, including 5 or less, e.g., 4.9 or less.

The uniform, rigid, spherical, nanoporous calcium phosphate particles employed in embodiments of the methods may be prepared using any convenient protocol. In one protocol of interest, the particles are manufactured by spray drying a slurry which includes nanoporous calcium phosphate (e.g., hydroxyapatite) crystals (which may range from 2 nm to 100 nm size range) to produce uniform spherical nanoporous calcium phosphate particles. The resultant particles are then sintered for a period of time sufficient to provide mechanically and chemically stable rigid spheres. In this step, the sintering temperatures may range from 100° C. to 1000°

C., such as 200° C. to 1000° C., such as 300° C. to 900° C. and including 300° C. to 800° C. for a period of time ranging from 1 hour to 10 hours, such as 2 hours to 8 hours and including 3 hours to 6 hours.

In some instances, the nanoporous calcium particles may be pre-treated. Pretreated particles may be prepared via a number of different protocols. In some instances, the particles may be neutralized with a pH adjuster, e.g., such as an acid. The pH may be adjusted to optimum range, which may be specific to the active agent, when necessary. Examples of pH adjusters of interest include weak or strong acids such as hydrochloric acid, glycolic acid, phosphoric acid, lactic acid and citric acid and others. In some instances, the particles may be pretreated with a phosphate salt, such as sodium phosphate or pretreated with a calcium salt, such as calcium chloride. In some instances, a mixture of buffering system is used such as sodium citrate and citric acid or calcium chloride and lactic acid. Where desired, any salts produced during this protocol may be removed, e.g., via filtering or decanting. Further details regarding pretreatment protocols of interest for nanoporous calcium phosphate particles may be found in U.S. Provisional Application Ser. No. 61/327,633.

Resveratrol Active Agent

The term "resveratrol active agent" refers an agent that has resveratrol activity. Examples of resveratrol active agents include, but are not limited to: resveratrol (3,4',5-Trihydroxystilbene or 3,4',5-Stilbenetriol or 3,5,4'-Trihydroxystilbene); as well as a derivative, metabolite or analogue thereof. The term "resveratrol, a derivative, metabolite or analogue thereof" as used herein comprises compounds encompassed by the general formula I:

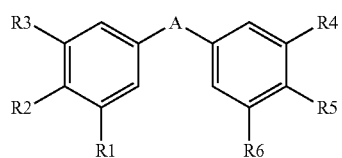

wherein A denotes a carbon-carbon single or double bond, the latter may be trans or cis, and R1, R2, R3, R4, R5 and R6, independently from each other denote hydrogen, hydroxy, etherified hydroxy or esterified hydroxy groups. Preferred are compounds I wherein A is a double bond (—CH=CH—). While the carbon-carbon double bond denoted by the symbol A may be trans or cis, formula I above is understood to also include cis/trans mixtures. Compounds of formula I wherein A is a trans carbon-carbon bond are employed in some instances.

Etherified or esterified hydroxy groups may be derived from unsubstituted or substituted, straight- or branched-chain alkyl groups having 1 to 26 carbon atoms or from unsubstituted or substituted, straight- or branched-chain aliphatic, araliphatic or aromatic carboxylic acids having 1 to 26 carbon atoms. Etherified hydroxy groups may further be glycoside groups, and esterified hydroxy groups may further be glucuronide or sulfate groups. Examples of compounds of formula I wherein A is —CH=CH— are resveratrol (R1, R3 and R5=hydrogen, R2, R4 and R6=hydroxy); piceatannol (R3 and R5=hydrogen, R1, R2, R4 and R6=hydroxy), and rhapontigenin (R5=hydrogen, R1, R3, R4 and R6=hydroxy, and R2=methoxy). Examples of compounds of formula I wherein A is —CH$_2$—CH$_2$— are dihydroresveratrol (R1, R3 and R5=hydrogen; R2, R4 and R6=hydroxy), dihydropiceatannol (R3 and R5=hydrogen; R1, R2, R4 and R6=hydroxy) and tristin (R3 and R5=hydrogen; R2, R4 and R6=hydroxy and R1=methoxy). These compounds are all well-known and commercially available or can be obtained in accordance with methods well-known in the art.

For the purposes of the invention, resveratrol, a derivative, metabolite or analogue thereof may be of synthetic or of natural origin. In one embodiment of the invention, resveratrol, particularly (trans)-resveratrol, of synthetic origin is used for the purposes of the invention. In another embodiment of the invention, resveratrol of natural origin is used, i.e., isolated from natural resveratrol sources, or as a resveratrol-containing extract from natural resveratrol sources such as grape seed extract or giant knotweed extract. Furthermore, resveratrol may be used for the purposes of the invention alone, i.e., as a single active component or in combination with one or more other active ingredients often used in nutritional supplemental formulations. Such other ingredients include, but are not restricted to, mineral salts; vitamins (e.g., vitamin E and C); carotenoids, such as β-carotene, lycopene, lutein or zeaxanthin; green tea catechins, such as epigallocatechin (EGCG); olive phenolics, such as hydroxytyrosol and oleuropein; Coenzyme Q10; genistein and PUFAs of all kinds, especially in the form of their esters, naturally occurring, in the form of extracts and concentrates or synthetically produced and in more or less pure form.

Resveratrol derivatives of interest further include, but are not limited to, those reported in United States Published Patent Application Nos. 20090035243, 20090035242, 20090035240 and 20090035236; the disclosures of which are herein incorporated by reference.

Solvent System

The solvent system may be made up of a single solvent or two or more different solvents, where the particular solvent or solvents making up the solvent system may be selected based on the nature of active agent to be complexed with the particles. In some instances, the solvent system is aqueous, and may be 100% water, or water in combination with one or more additional solvents, including polar and non-polar solvents, which may be organic or inorganic, as desired. In other instances, the solvent system may be non-polar.

Fabrication of Dry Particulate Actives

As summarized above, in preparing dry particulate actives in accordance with embodiments of the invention, the active agent(s), nanoporous calcium phosphate particles and a solvent system are combined to produce a calcium phosphate particles/active agents mixture. The various components may be combined using any convenient protocol. In some instances, the active agent(s) is first dissolved in the solvent system, and then the resultant active agent solution is combined with an amount of calcium phosphate particles. In yet other instances, the calcium phosphate particles are combined first with the solvent system, and then the active agent is added to produce the calcium phosphate particles/active agent(s) mixture.

The active agent(s) and solvent system may be combined using any protocol sufficient to produce the desired mixture solution. In some instances, the active agent(s) and solvent system are combined with agitation. Agitation may be provided using any convenient protocol, e.g., stir bar, agitation blade, propeller, etc. The temperature at which the active is combined with the solvent system and dissolved therein may vary, and may be below room temperature, at room temperature or above room temperature. The specific temperature at which the combination of active agent and solvent is carried out may be chosen based on the nature of the active agent (such that a temperature is chosen that will not inactivate the active agent) as well as the properties of the solvent system, e.g., melting point, boiling point, etc. In some instances, the temperature ranges from just above 0° C. to 200° C. In some instances, the temperature ranges from 4 to 25° C., e.g., 5 to 10° C. In some instances, the temperature is above room temperature, e.g., 35 to 60° C., e.g. 40 to 45° C., 50 to 55° C., or higher. In some instances, the temperature ranges from 65 to 150° C., e.g. 70 to 85° C., 90 to 105° C., 120 to 135° C. or higher. In some instances, the temperature ranges from 5 to 80° C., such as 5 to 75° C., e.g., 10 to 65° C., e.g., 20 to 60° C.

The amount of active agent that is dissolved in the solvent system may be selected based on the solubility of the active agent in the solvent system and/or based on the amount of calcium phosphate particles to be used. In some instances, the amount of active agent relative to the calcium phosphate particles is 0.1% by weight or more, such as 10% by weight or more, such as 20% by weight or more, such as 30% by weight or more, such as 40% by weight or more, such as 60% by weight or more, such as 70% by weight or more, such as 80% by or more, such as 90% by weight or more, including 100% by weight or more, including 1000% by weight or more. In some instances, the weight ratio of active agent(s) to calcium phosphate particles ranges from 0.01:10, 0.1:1, 1:1 and 1:0.1. In some instances, the weight ratio of active agent(s) to calcium particles ranges from 0.5:1.0 to 5:1, where in some instances the ratio is 1:1.

Following preparation of the active agent solution, e.g., as described above, a suitable amount of calcium phosphate particles (which may or may not be pre-treated, e.g., as described and referenced above) is combined with the solution. In some instances, the calcium phosphate particles that are combined with the active agent solution are dry. In some instances, the methods include wetting an initial amount of nanoporous calcium phosphate particles with a solvent system, where the solvent system may be the same as or different from that used to prepare the active agent solution, e.g., as described above.

The particles (either dry or wetted as described above) may be combined with a solution of an active agent present in a solvent system, e.g., as described above, to produce a liquid composition that includes particles and an active agent(s) in a solvent system, which composition may be referred to herein as an active agent mixture. The active agent solution and particles (dry or wetted, as desired) may be mixed using any convenient protocol, e.g., with agitation (such as described above), to produce a liquid composition that includes both the particles and the active agent in a solvent system. This mixing step lasts for a time sufficient to produce the desired mixture, and in some instances ranges in length from 1 minute to 600 minutes, such as 5 minutes to 300 minutes. In certain instances, the nanoporous calcium phosphate particles and active agent(s) solution are combined under negative pressure. When combined under negative pressure, pressures of interest may vary and in some instances range from 0.001 torr to 1 torr, such as 0.01 torr to 0.1 torr and including 0.05 torr to 0.5 torr.

Following preparation of the mixture, the solvent system is dried off from the active agent mixture to produce the desired fine dry particulate active. Drying may be accomplished using any convenient protocol, where protocols of interest include, but are not limited to: maintaining at elevated temperatures sufficient to evaporate the solvent. Drying methods of interest include, but are not limited to: drying by heat convection, such as spray drying, air flow drying, fluid bed drying, and super-heated steam drying, or drying by heat conduction, such as vacuum drying, freeze drying, rotary drum drying, and rotary vacuum drying or drying by heat radiation, such as infrared heat drying and microwave drying, or heat radiation with other electromagnetic waves, and or other methods such as super critical drying, etc. Combinations of various protocols may be employed, as desired. Following separation of the solvent, the resultant dry product may be further processed as desired, e.g., the product may be grinded, milled (e.g., via ball mill, hammer mill, jet impact mill, wet impact mill, etc.), sieved (e.g., with or without vibration, subjected to air-flow or jet-flow classification), etc., as desired, to produce a fine dry particulate active.

As indicated above, the active compositions of the invention may be characterized by having a single active agent associated with given calcium particles, or two or more active agents (e.g., three or more active agents, four or more, five or more) different active agents associated with the same calcium particles.

The above fabrication protocol results in the production of a fine dry particulate resveratrol active of the invention. In the resultant dry powder active agent is present inside of the particles, and/or bound to the particles, covalently or ionically, and/or on the surface of the particles, and/or tightly associated with the particles and loosely associated with the particles. The amount of active agent component (which is made up of one or more distinct active agents) that is bound or associated with calcium phosphate particles may vary depending on the particular active agent(s). The resultant active particulate has a distribution of diameter of the particles, where in some instances the majority (such as 60% or more, 75% or more, 90% or more, 95% or more) of the particles have diameters that range from 0.01 to 100 μm, such as from 0.01 to 20 μm, such as from 0.1 to 10 μm, and including from 0.1 to 2 μm.

In some instances, the amount of active agent relative to the calcium particles ranges from 1% or less by weight to 500% by weight or more, e.g., in some instance being 50% by weight or more, such as 60% by weight or more, such as 70% by weight or more, such as 80% by or more, such as 90% by weight or more, including 100% by weight or more, such as 150% by weight or more, e.g., 500% by weight or more, including 1000% by weight or more. In some instances, the weight ratio of active agent(s) to calcium particles ranges from 0.5:1.0 to 5:1, e.g., 0.1 to 1 to 1:0.1, where in some instances the ratio is 1:1.

Depending on the nature of the resultant active to be employed, the protocols may or may not include a step of coating the resultant active powder. Coating materials (which may include one or more coating material) of interest are those that preserve the association of the active agent with the calcium phosphate particles in various formulations, e.g. formulations designed for topical application to the skin. Suitable coating agents include agents that are physiologically acceptable and are solid at room temperature and are suitable for application to the skin. The coating material component may be a single material or a combination of two or more materials, e.g., where the combination provides for one or more desirable properties. Materials that find use as coating materials include, but are not limited to waxes, butters, etc. Coatings materials of interest and methods for their use are further described in U.S. patent application Ser. No. 12/565, 687 published as US 2010-0086606 A1; the disclosure of which is herein incorporated by reference.

When employed, the coating component or stabilizer component may be a single material or a combination of two or more materials, e.g., where the combination provides for one or more desirable properties, such as desired melting temperature, etc. Materials that find use as stabilizers include, but are not limited to: Acrocomia Aculeata Seed Butter, Almond Butter, Aloe Butter, Apricot Kernel Butter, Argan Butter, Attalea Maripa Seed Butter, Avocado Butter, Babassu Butter, Bacuri Butter, Bagura Soft Butter, Baobab Soft Butter, Bassia Butyracea Seed Butter, Bassia Latifolia Seed Butter, Black Currant Seed Butter, Brazil Nut Butter, Camelina Butter, Camellia Butter, Candelilla Butter, Carnauba Butter, Carpotroche Brasiliensis Seed Butter, Chamomile Butter, Cocoa Butter, Coconut Butter, Coffee Butter, Cotton Soft Butter, Cranberry Butter, Cupuacu Butter, Grape Seed Butter, Hazel Nut Butter, Hemp Seed Butter, Horsetail Butter, Illipe Butter, Irvingia Gabonensis Kernel Butter, Jojoba Butter, Karite Butter, Kokum Butter, Kukui Butter, Lavender Butter, Lemon Butter, Lime Butter, Macadamia Butter, Mango Butter, Marula Butter, Monoi Butter, Mowrah Butter, Mucaja Butter, Murumuru Butter, Olea Butter, Olive Butter, Orange Butter, Palm Oil, Passion Butter, Phulwara Butter, Pistachio Butter, Pomegranate Butter, Pumpkin Butter, Raspberry Butter, Rice Butter, Sal Butter, Sapucainha Butter, Seasame Butter, Shea Butter, Soy Butter, Tamanu Butter, Sunflower Seed Butter, Sweet almond Butter, Tangerine Butter, Tucuma Seed Butter, Ucuuba Butter, Wheat Germ Butter, acrawax, bayberry wax, beeswax, candelilla wax, castor wax, carnauba wax, ceresin wax, esparto wax, glycowax, jojoba wax, Japan wax, lignite wax, linear polyethylene wax, microcrystalline petroleum wax, montan wax, ouricouri wax, ozokerite wax, paraffin wax, rice bran wax, shellac wax, silicone waxes, synthetic waxes, sugarcane wax, petrolatum, hard tallow, cetyl alcohol, lanolin alcohol, lanolin, stearyl alcohol, stearone, glyceryl monostearate, glyceryl distearate, glycerol palmitostearate, cetyl palmitate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene homopolymers, ethylene-propylene copolymers, ethylene-hexene copolymers, ethylene glycol methacrylate, and/or polyethylene glycols, such as PEG-18, PEG-20, PEG-32, PEG-75, PEG-90, PEG-100, and PEG-180.

Topical Formulations

Aspects of the invention further include topical formulations that are configured for application to a topical site of a human subject. Topical formulations of the invention are for applications such as mucosal surface or keratinized skin surface of a mammalian subject, such as a human subject. By mucosal surface is meant a location of a subject that includes a mucosal membrane, such as the inside of the mouth, in the inside of the nose, etc. By keratinized skin surface is meant a skin location of a subject, i.e., a location of the external covering or integument of an animal body. Because the topical formulations of the invention are formulated for delivery to topical location, they are formulated so as to be physiologically compatible with the topical location for which they are formulated. Accordingly, when contacted with the target keratinized skin surface for which they are formulated, the topical compositions of certain embodiments do not cause substantial, if any, physiological responses (such as inflammation or irritation) that would render the use of the topical compositions unsuitable for topical application. Topical formulations of the invention include: (a) an amount of the actives (which may or may not be stabilized); and (b) a topical delivery vehicle.

As indicated above, the topical compositions include an amount of the fine dry particulate active present in a topical delivery vehicle. The amount of fine dry particulate active that is present in the delivery composition and therefore combined with a delivery vehicle may vary. In some embodiments, the amount of fine dry particulate active present in the delivery vehicle ranges from 0.01 mg/g to 500 mg/g, such as 0.01 to 250 mg/g, such as 0.1 to 200 mg/g, e.g., 1 to 100 mg/g, including 10 to 50 mg/g fine dry particulate active per gram of delivery vehicle. In certain embodiments the fine dry particulate active are present in compositions in an amount ranging from about 0.001% or more by weight, such as 0.01%, or 0.05%, or 1% or more, 5% or more, 10% or more, 15% or more, 25% or more, 30% or more 50% or more. In certain embodiments, the fine dry particulate active is added directly to the delivery vehicle (i.e., the fine dry particulate active is not wetted prior to combining/mixing with the delivery vehicle). In other words, the fine dry particulate active and the delivery vehicle are combined to form the topical composition.

The delivery vehicle (i.e., topical delivery component) refers to that portion of the topical composition that is not the fine dry particulate active. Delivery vehicles of interest include, but are not limited to, compositions that are suitable for applications via one or more of oral, topical, implantation, ocular, aural, rectal, vaginal, etc., routes. In certain embodiments, the vehicle is formulated for application to a topical region or surface of a subject, such as a keratinized skin surface. The subject compositions may be formulated as stable solutions or suspensions of the components, e.g., in an aqueous solvent. Where desired, the components may be combined with one or more carrier materials to form a solution, suspension, gel, lotion, cream, ointment, aerosol spray, roll-on, foam products, mousses, powders, sticks, or the like, as desired. Of interest in certain embodiments are aqueous delivery vehicles, i.e. aqueous vehicles that include a certain amount of water. Examples of aqueous vehicles include hydrogel vehicles, sprays, serums, etc.

The topical composition may also contain other physiologically acceptable excipients or other minor additives, particularly associated with organoleptic properties, such as fragrances, dyes, buffers, cooling agents (e.g. menthol), coating materials or the like. The excipients and minor additives will be present in conventional amounts, e.g., ranging from about 0.001% to 5%, such as 0.001-2%, by weight, and in some instances not exceeding a total of 10% by weight.

Lotions (as well as other topical formulations) of interest may include one or more of the following components: Water, Viscosity modifiers, Humectants, Vegetable oils and hydrogenated vegetable oils, Emollients, Conditioning Agents, Emulsifiers, Glyceryl Esters of Fatty Acids, Silicone, C1-C30 monoesters and polyesters of sugar, Conditioning Agents, Preservatives, etc. Depending on the topical formulation, additional components of interest include: Abrasives, Absorbents, Antimicrobial and antifungal agents, Astringents, Anti-Acne agents, Anti-wrinkle agents, Anti-oxidants, Antimicrobials, Binders, Biological actives, Buffering actives, Bulking actives, Chelating agents, Chemical additives, External analgesics, Film former agents, Opacifying agents, pH adjusters, Reducing agents, Colorants, Fragrances, Cosmetic Soothing Agents, Tanning actives & accelerators, Skin lightening/whitening agents, Sunscreens, Surfactants, Skin Conditioning Agents, Vitamins, etc.

As indicated above, of interest in certain embodiments are semi-solid delivery compositions, such as gels, creams and ointments. Such compositions may be mixtures of (in addition to the active agent) water, water soluble polymers, preservatives, alcohols, polyvalent alcohols, emulsifying agents, wax, solvents, thickeners, plasticizers, pH regulators, water-retaining agents and the like. Furthermore, such compositions may also contain other physiologically acceptable excipients or other minor additives, such as fragrances, dyes, buffers, coating materials or the like.

Also of interest are solid formulations, such as topical patch formulations. Topical patch formulations may vary significantly. Topical patch formulations may include an active agent layer, a support and a release liner. The active agent layer may include physiologically acceptable excipients or other minor additives, such as fragrances, dyes, buffers, coating materials or the like. The support may be made of a flexible material which is capable of fitting in the movement of human body and includes, for example, plastic films, various non-woven fabrics, woven fabrics, spandex, and the like. Various inert coverings may be employed, which include the various materials which may find use in plasters, described below. Alternatively, non-woven or woven coverings may be employed, particularly elastomeric coverings, which allow for heat and vapor transport. These coverings allow for cooling of the pain site, which provides for greater comfort, while protecting the gel from mechanical removal. The release liner may be made of any convenient material, where representative release films include polyesters, such as PET or PP, and the like.

When present in the delivery vehicle, a high weight percentage of the active agent of the initial fine dry particulate composition may remain associated with the calcium particles. In some instances, the weight percentage that remains associated with the calcium particles (and therefore is not free in the delivery vehicle) is 40% or more, such as 50% or more, including 60% or more, e.g., 70% or more. Active agent that remains associated with the calcium particles may be carried along with the particles into the skin for delivery in the acidic environment of the skin.

Utility

Topical formulations of the invention find use in methods of delivering active agents to a topical location of a subject, where the topical location may be a skin surface location or a mucosal location. In delivering active agents to a topical location of a subject, formulations of the invention may deliver the active agent at least into an epidermal location that is beneath the skin surface of a subject. As such, embodiments of the invention include methods of delivering active agent/calcium particle complexes into the stratum corneum of a subject, where the methods may result in delivery of the complexes into the deep stratum corneum and/or dermis of a subject. By “deep stratum corneum” is meant a region that is 1 or more cell layers below the skin surface, such as 2 or more, e.g., 5 or more cell layers below the skin surface, including 10 or more cell layers below the skin surface. In some instances, the active agent/calcium particle complexes are delivered to region of the stratum corneum that is 2 μm or more such as 5 μm or more and including 15 μm or more below the surface of the skin.

Upon reaching their target dermal location, the active agent/calcium particle complexes may begin to release their active agent “payload” and break down (e.g., via dissolution caused by pH gradient of the skin), as the uniform, rigid, spherical, nanoporous particles dissolve under acidic conditions, e.g., conditions of pH 5.5 or lower, such as 5 or lower, including 4.0 or lower, such as the physiological acidic conditions of the stratum corneum. The time required for dissolution of particles in the stratum corneum may vary, and in certain embodiments ranges from a few minutes up to several days, such as 1 minute to 24 hours, such as 10 minutes to 12 hours and including 30 minutes to 3 hours, over which time period active agent is released from the fine particulate dry active. The proportion of active agent that is released from the active agent/calcium particle complexes may vary, and in certain instances is 0.01% or more, such as 0.1% or more, including 1% or more, such as 10% or more, including 50% or more, 75% or more, including up to 100% (w/w).

Methods of the invention may therefore result in delivery of an active agent at least into the stratum corneum of a subject. Additional target locations of the body of interest include additional epidermal regions, such as but not limited to the stratum lucidum, stratum granulosum, stratum spinusom, stratum basale and dermis. In certain embodiments, the active agent is delivered to a region of the dermis. In certain embodiments, the active agent is delivered to a region below the dermis, e.g., into sub-cutaneous tissues.

In practicing methods of the invention, a topical formulation is applied to a topical region of a subject and maintained at the topical region for a period of time sufficient to result in the desired delivery of active agent to the subject, as described above. The topical region is, in certain embodiments, a keratinized skin region. The keratinized skin region, including hair follicles, sweat glands and sebaceous glands, may be present at a variety of locations, e.g., limbs, arms, legs; torso, e.g., chest, back, stomach; head, e.g., neck, face; etc. In certain embodiments, the region will be a head region, such as a facial region, e.g., forehead, occipital region, around the mouth, etc. The topical region to which the composition is applied may vary with respect to area, ranging in certain embodiments from 1 $mm^2$ to 20,000 $cm^2$ or more, such as from 1 to 50 $cm^2$, and including from 3 to 10 $cm^2$.

Following application, the topical formulation is maintained at the site of application for a period of time sufficient for a desired therapeutic outcome to occur, e.g., amelioration of a symptom(s) of interest, reducing dryness. The period of time may vary, and in certain embodiments ranges from instantaneously up to several days, such as 1 min to 24 hours or longer, such as from 30 min to 12 hours and including from 1 hour to 12 hours or longer.

In practicing the methods of the invention, a subject may be administered a single dose or two or more doses over a given period of time. For example, over a given treatment period of one month, 1 or more doses, such as 2 or more doses, 3 or more doses, 4 or more doses, 5 or more doses, etc., may be administered to the subject, where the doses may be administered weekly or daily or even multiple times per day, with a holiday period in between, e.g., where the holiday period may vary, e.g., 4 hours, 6 hours, 12 hours, 1 day, 3 days, 7 days, etc.

The subject methods and compositions may be used in a variety of different kinds of animals, where the animals are typically “mammals” or “mammalian,” where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects or patients are humans.

The subject topical formulations find use in applications where it is desired to deliver a resveratrol active agent to a subject. In certain embodiments, the subject topical formulations are employed in the treatment of a skin condition. By “treatment” is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition. In certain embodiments a subject may be diagnosed for the presence of the disease condition, such that the topical formulations are provided to a subject known to be suffering from the disease condition.

Practice of methods of the invention can enhance result in the improvement in skin, when there is a noticeable decrease in the amount of wrinkling, roughness, dryness, laxity, sallowness, or pigmentary mottling of the treated skin. Methods of measuring improvements in skin condition are well known in the art (see, e.g., Olsen et al., J. Amer. Acad. Dermatol. 26:215-24, 1992), and can include subjective evaluations by the patient or a second party, e.g., a treating physician. Objective methods can include skin topography measurements, such as those described in Grove et al., J. Amer. Acad. Dermatol. 21:631-37 (1989). In skin topography measurements, silicone rubber replicas are made of a small area of skin, e.g., a 1 cm diameter circular area. The silicone rubber replicas capture fine lines and wrinkles on the skin. These specimens are then analyzed using computerized digital image processing to provide an objective measurement of the skin's topography. Skin topography measurements generated following digital-image processing can be measured using the values $R_a$ and $R_z$ as described in Olsen et al., J. Amer. Acad. Dermatol. 37:217-26, 1997, where $R_a$ represents the area of deviation of skin surface features above and below an average central line, and $R_z$ represents the difference between the maximum and minimum heights in five equal segments of the skin surface profile. A statistically significant decline (e.g., $P<0.05$) in $R_a$ and $R_z$ values in skin treated according to the presence invention compared to untreated skin indicates an improvement in skin, as is achieved by practicing the methods of the invention.

Use of the compositions and methods of the invention provides for a number of important advantages. In some instances, the topical formulations (e.g., creams and lotions) that include the fine dry particulate resveratrol active agent compositions are storage stable, such that the composition and/or active agent properties, e.g., color, viscosity, active gent activity, etc., are not substantially altered over extended periods of time, e.g., 1 week or longer, 2 weeks or longer, 1 month or longer, 6 months or longer, 1 year or longer, under room and elevated temperatures, e.g., 40° C. or greater, including 50° C. or greater. In some instances, the topical formulations (e.g., creams and lotions) that include the fine dry particulate resveratrol active agent compositions exhibit increased bioavailability of the active agent as compared to a control, where the magnitude of increase may be 2 fold or greater, such as 5 fold or greater, including 10 fold or greater. In some instances, the topical formulations (e.g., creams and lotions) that include the fine dry particulate resveratrol active agent compositions exhibit sustained release of the active agent, where by sustained release is meant release of therapeutically desired amount for 6 hours or longer, such as 12 hours or longer, including 18 hours or longer, e.g., 24 hours or longer, including 2 days or longer, e.g., 3 days or longer, 4 days or longer, 5 days or longer, 6 days or longer, 7 days or longer. In some instances, the topical formulations (e.g., creams and lotions) that include the fine dry particulate resveratrol active agent compositions exhibit synergist results with respect to the skin health activity of resveratrol and calcium, where the magnitude of therapeutic results is greater than the expected additive activity of these two agents individually.

The following examples are offered by way of illustration and not by way of limitation.

Experimental

I. Preparation of resveratrol-Hydroxysomes 1 g of resveratrol powder was dissolved in 20 mL of ethanol, and then add 1 g of Hydroxysomes® calcium phosphate particles (Laboratory Skin Care, South San Francisco) powder in a 50 mL rotary evaporating flask. The mixture in the flask was set to a rotary vacuum evaporator, and the ethanol was removed at 60° C. in vacuum for 2 hours. The resultant product was tested for shelf life stability. The product was observed to be stable at room temperature for 24 months, 40° C. for 3 months and 50° C. for 1 month as determined using an HPLC protocol.

In addition, several formulations of the fine dry particulate composition of resveratrol of the invention were tested in water based topical formulations. In these formulations, less than 15%, including less than 10%, of the resveratrol was released from the Hydroxysomes® calcium phosphate particles. Using HPLC analysis, the product was observed to be stable in the formulation at room temperature, at 40° C. for 3 months and 50° C. for one month. No change in pH, color, appearance or viscosity was observed.

II. Topical Delivery

A fine dry particulate composition of resverstrol as described above was combined with a cream topical delivery vehicle and applied to human skin. Delivery of stable resveratrol to stratum corneum was achieved without any disruption to the integrity of the skin, and at much higher levels when compared to the two leading commercial resveratrol creams (control 1 and control 2). Research studies show that the amount of resveratrol released from the fine dry particulate composition of resverstrol of the invention in the skin is at much higher concentration than controls when equal amounts of each product were applied to the forearm of the a human subject for 2, 8 and 24 hours.

Specifically, two commercial resveratrol skin products (micronized resveratrol and phosphorylated resveratrol) were compared with a fine dry particulate composition as described above in a human subject. Equimolar amounts of the three formulations were applied to the forearm of a human subject for 2, 8 and 24 hours. After each time point, the skin surface was cleaned and 5 tape strips obtained from each application site. At each time point, the invention was found at higher concentrations in the skin. The results are shown in FIG. 1.

III. Coated Compositions 1 g of polyethylene wax, performalene obtained from new phase technologies, USA, was dissolved in 20 mL of Hexane. 1 gram of resveratrol-Hydroxysomes powder prepared as described above was added to the Eudragit in acetone solution, and mixed until the suspension is uniform. The suspension was spray dried using a B-290 spray dryer, BUCHI Labortechnik AG in Flawil, Switzerland, at 60 degree C. of the temperature in drying chamber.

The coating material may be selected from the group comprising fats, oils, waxes, resins, emulsifiers or mixtures thereof. In some instances, the shell material is selected from the group comprising animal oils and fats, fully hydrogenated vegetable or animal oils, partially hydrogenated vegetable or animal oils, unsaturated, hydrogenated or fully hydrogenated fatty acids, unsaturated, partially hydrogenated or fully hydrogenated fatty acid monoglycerides and diglycerides, unsaturated, partially hydrogenated or fully hydrogenated esterified fatty acids of monoglycerides or diglycerides, unsaturated, partially hydrogenated or fully hydrogenated free fatty acids, other emulsifiers, animal waxes, vegetable waxes, mineral waxes, synthetic waxes, natural and synthetic resins and mixtures thereof.

Animal oils and fats are such as, but not restricted to, beef tallow, mutton tallow, lamb tallow, lard or pork fat, sperm oil. Hydrogenated or partially hydrogenated vegetable oils are such as, but not restricted to, canola oil, cottonseed oil, peanut oil, corn oil, olive oil, soybean oil, sunflower oil, safflower oil, coconut oil, palm oil, linseed oil, tung oil and castor oil. Free fatty acids are such as, but not restricted to, stearic acid, palmitic acid and oleic acid. Other emulsifiers are such as, but not restricted to, polyglycerol esters, sorbitan esters of fatty acids. Animal waxes are such as, but not restricted to, beeswax, lanolin, shell wax or Chinese insect wax. Vegetable waxes are such as, but not restricted to, carnauba, candelilla, bayberry or sugarcane waxes. Mineral waxes are such as, but not restricted to, paraffin, microcrystalline petroleum, ozocerite, ceresin or montan.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A fine dry particulate resveratrol composition that includes a resveratrol active agent(s) present inside of the pores of nanoporous calcium particles and/or on the surface of the particles and/or loosely associated with the particles.

2. The fine dry particulate resveratrol composition according to claim 1, wherein the nanoporous calcium particles are nanoporous calcium phosphate particles.

3. The fine dry particulate resveratrol composition according to claim 2, wherein the nanoporous calcium phosphate particles are uniform, rigid, spherical, nanoporous calcium phosphate particles.

4. The fine dry particulate resveratrol composition according to claim 3, wherein the uniform, rigid, spherical, nanoporous calcium phosphate particles are ceramic.

5. The fine dry particulate resveratrol composition according to claim 1, wherein the uniform, rigid, spherical, nanoporous calcium phosphate particles have a diameter ranging from 1 to 10 μm.

6. The fine dry particulate resveratrol composition according to claim 5, wherein the uniform, rigid, spherical, nanoporous calcium phosphate particles have a diameter of 2 μm or less.

7. The fine dry particulate resveratrol composition according to claim 1, wherein the nanoporous calcium phosphate particles comprise pores ranging in size from 2 nm to 100 nm.

8. The fine dry particulate resveratrol composition according to claim 1, wherein the resveratrol active agent is 3,4',5-Trihydroxystilbene resveratrol.

9. A topical formulation comprising:
    dry particulate resveratrol composition according to claim 1; and
    a topical delivery vehicle.

10. The topical composition according to claim 9, wherein the topical delivery vehicle is an aqueous topical delivery vehicle.

11. A method of delivering a resveratrol active agent to a subject, the method comprising:
    applying a topical formulation comprising:
        (a) a fine dry particulate resveratrol composition according to claim 1; and
        (b) a topical delivery vehicle;
    to a topical region of the subject to deliver the resveratrol active agent to the subject.

* * * * *